(12) United States Patent
Garrard et al.

(10) Patent No.: US 6,713,766 B2
(45) Date of Patent: Mar. 30, 2004

(54) GAMMA CAMERA WITH CAPABILITY OF MODIFYING STUDY DURING EXAM

(75) Inventors: Jody L. Garrard, Elk Grove, CA (US); Horace Hines, San Jose, CA (US); Hugo Bertelsen, Aalborg (DK); David E. Coles, San Francisco, CA (US); Jeffrey A. Hallett, Livermore, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 305 days.

(21) Appl. No.: 09/895,425

(22) Filed: Jun. 28, 2001

(65) Prior Publication Data

US 2003/0001097 A1 Jan. 2, 2003

(51) Int. Cl.[7] .................................................. G01T 1/00
(52) U.S. Cl. .............................. 250/363.02; 250/363.01
(58) Field of Search ....................... 250/363.02, 363.01, 250/361 R, 458.1

(56) References Cited

U.S. PATENT DOCUMENTS 5,459,769 A    10/1995  Brown
6,084,939 A  *  7/2000  Tamura .................... 378/98.2
6,224,549 B1    5/2001  van Drongelen
6,425,865 B1 *  7/2002  Salcudean et al. .......... 600/437
2003/0004584 A1 * 1/2003 Hallett ........................ 700/17
2003/0042423 A1 * 3/2003 Bertelsen .................... 250/369

FOREIGN PATENT DOCUMENTS

WO     WO 97/21113     6/1997

* cited by examiner

Primary Examiner—David Porta
Assistant Examiner—Christine Sung
(74) Attorney, Agent, or Firm—Eugene E. Clair, Esq.

(57) ABSTRACT

A gamma camera is provided in which the study protocol can be modified after the study has commenced and while event data is being acquired. In such a camera, study parameters such as the duration of the study, the number of image frames acquired, or the count criterion required to produce an image may be changed dynamically as the study proceeds. Thus, a nuclear study which is seen to be leading to unsatisfactory or less than optimal results may be altered during acquisition to increase the likelihood that diagnostically useful results will be produced.

11 Claims, 5 Drawing Sheets

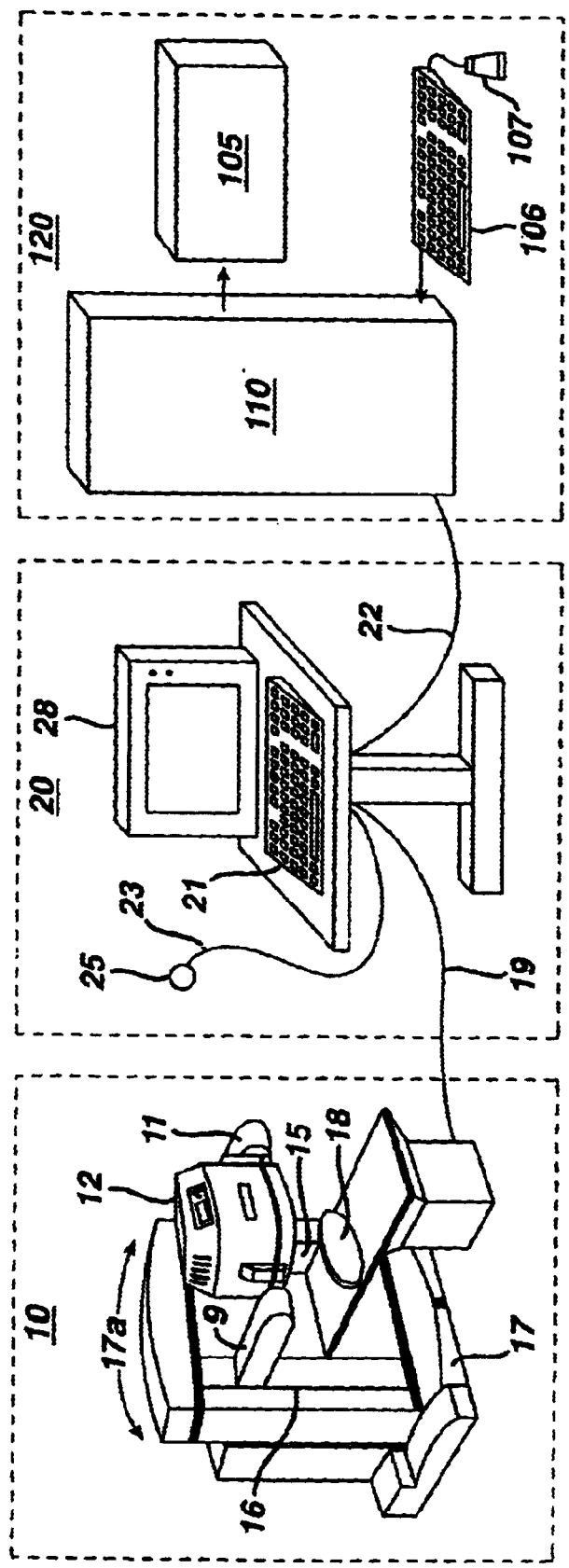

FIG. 2

Procedure ID: Gated Spect — 300
Spect Parameters

Degrees in Orbit: 301
Images in Orbit: 303
Matrix Size: 305
Starting Location: 307
Rotation Direction: 309
Orientation: 311
Orbit (circular): 313
Flood Correction: 315
Acquisition Method: 317

Isotope ID: 351
Patient ID: 353
View ID: 355

Processing 357

Gated Parameters

No. of Gated Frames 331
% R-R Interval Variance
 Max % Window 333
 Min % Window 335
R-R Interval Fixed 337
R-R Interval Vary 339
No. Exclude After Variance 341
Time Per ECT Azimuth or Total Beats 343

Time _____ Avg R-R _____
Frame No. _____ Gated Frames _____
Max Frame _____ Max Frames _____
Counts/Sec _____
Beats _____
                                        365

GAMMA CAMERA WITH CAPABILITY OF MODIFYING STUDY DURING EXAM

This invention relates to gamma cameras by which studies can be performed that produce diagnostic images using radioisotopes and, in particular, to gamma cameras which provide the ability to modify the parameters of a study while the image data is being acquired.

In preparing for a nuclear medicine study the clinician will spend time setting up the nuclear camera so that it will proceed through the sequence of steps needed to carry out the study. During the setup procedure the clinician will establish parameters which govern the study, such as the time during which emission events are acquired, the number of image frames that will be acquired and produced, and the number of event counts minimally required to produce a reliable image. After all the necessary parameters have been set and the patient has been prepped, the examination will begin and the gamma camera executes the study defined by the parameters. The study is concluded when the gamma camera has performed the procedures governed by all the parameters.

However, as the study proceeds the clinician may observe that the data is not being acquired as anticipated. The uptake of the radioisotope by the body may not be proceeding as rapidly or as slowly as expected, for instance, or the washout of the radioisotope from the region of interest may not be proceeding at the rate anticipated. In such cases the images produced may be inadequate to make a definitive diagnosis. Now armed with this experience, the clinician will generally conduct a second study using parameters which accommodate the shortcomings of the first study. In doing so the clinician must hope that the physiological conditions experienced in the first exam will be repeated so that yet a further imaging session is not required. But the second study may disrupt the scheduling of patients for the camera, may require a second appointment by the patient, and exposes the patient to the radioisotope a second time. It would be desirable to prevent these difficulties by enabling the clinician to react during the study so that corrections in the study protocol can be made while the study is in progress and the need for repeat studies prevented.

In accordance with the principles of the present invention, a gamma camera is provided in which the study protocol can be modified after the study has commenced and while event data is being acquired. In such a camera study parameters such as the duration of the study, the number of image frames acquired, or the count criterion required to produce an image may be changed as the study proceeds. Thus, a nuclear study which is seen to be leading to unsatisfactory or less than optimal results may be altered during acquisition to increase the likelihood that diagnostically useful results will be produced.

IN THE DRAWINGS

FIG. 1 illustrates the major components of a gamma camera system;

FIG. 2 illustrates some of the parameters which may be used in a gated SPECT study;

Figure 3:
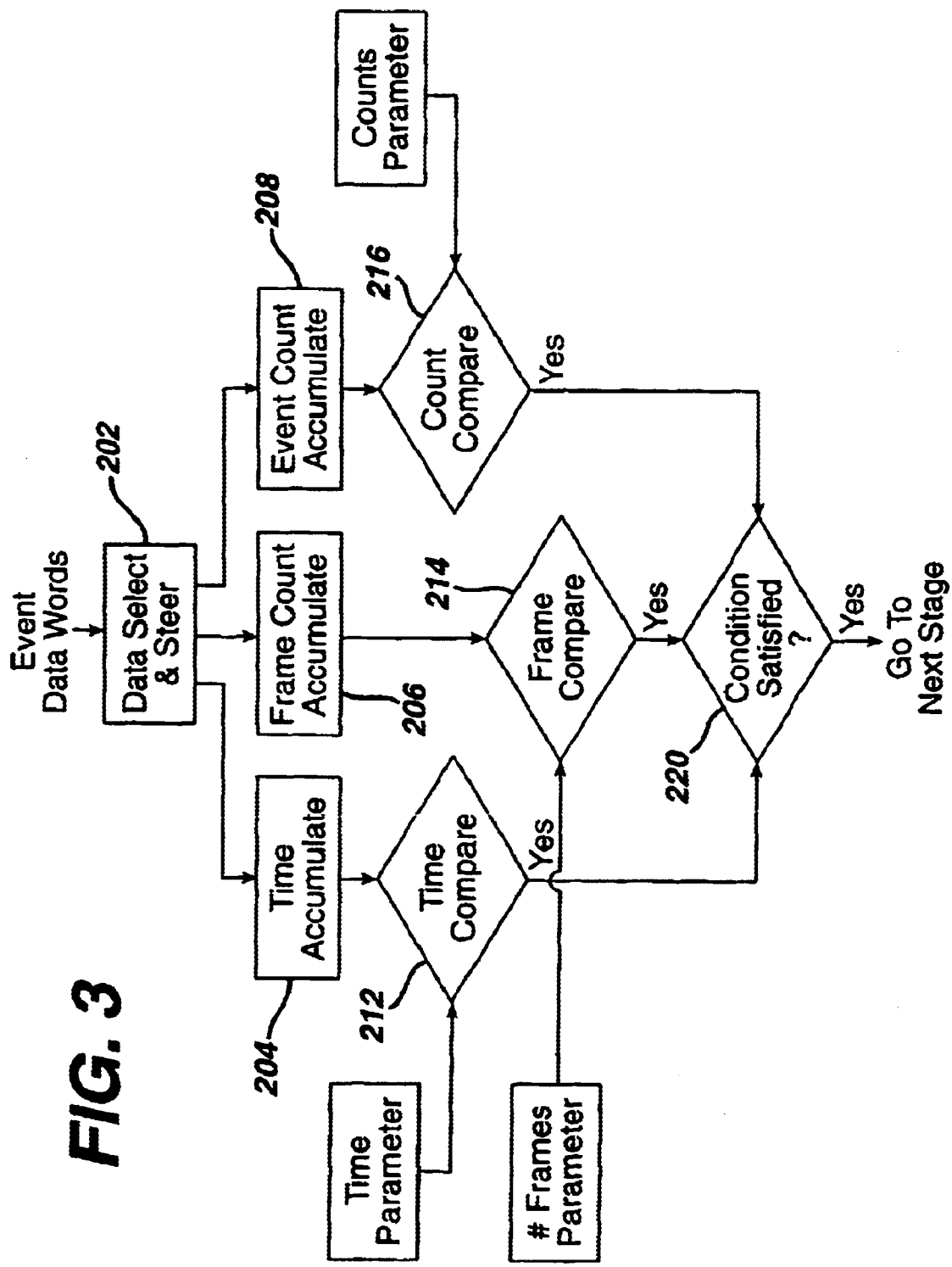
FIG. 3 is a flowchart illustrating the execution of a gamma camera study with variable parameters in accordance with the present invention.

FIG. 1 illustrates the major components of a nuclear camera image acquisition, processing and display system. The present invention includes either a single head (single detector) camera 10 as shown in the drawing or a dual head (dual detector) camera as shown in U.S. Pat. No. 5,760,402 (Hug. et al.) or U.S. Pat. No. 6,150,662 (Hug et al.). These camera systems are SPECT cameras ideal for cardiac, abdominal, and whole body studies and are capable of implementing gated SPECT imaging techniques. The dual detector systems may also be used to conduct PET studies. In the illustration of FIG. 1, two arms 11 and 9 mounted on vertical tracks 16 and 15 form a gantry structure that can move the detector head 12 in various projection angles to accomplish the required 180 and 360 degree movements of the detector 12 used in gated SPECT studies. Pivot structure 17 allows the camera detector 12 and gantry structure to pivot clockwise or counterclockwise. The camera system 10 includes a detector head 12 comprising a number of well known radiation detection components of the Anger camera type including a photomultiplier array, a collimator, a scintillating crystal and a digital pixel output. The camera system 10, in a well known fashion, images the patient to provide digital image data which is binned according to particular discrete angles of rotation in which the detector 12 traverses about the patient. Binning can also occur according to particular phases of the cardiac cycle (R—R interval, defined below). For each angle of rotation, several phases of the cardiac cycle may be interrogated. Particular (x,y) coordinate positions within the imaging detector of the camera system are called pixel locations and the number of scintillations detected by each pixel location is represented by a count value for that pixel. Each pixel contains a count value representing the number of radiation emissions detected at that location of the detector 12. The resulting digital image data from the camera system 10 is binned according to the particular discrete angle of rotation in which the detector was situated when the image data was acquired. Also binned is the gated segment (phase) within the R—R interval in which the data was acquired in gated SPECT studies. The pixel matrix of (x,y) locations is referred to herein as a histogram of scintillations at these coordinate locations. It is understood that a histogram represents a raw image. For example, a typical detector 12 may have a resolution of (64×64) pixels or (128×128) pixels available for imaging and is capable of imaging at a maximum resolution of approximately (1000×1000) pixels.

The camera system 10 is coupled to a data acquisition computer system 20, which in a particular constructed embodiment is implemented using a general purpose computer system having high speed communications ports for input and output coupled to a two-way data transmission line 19 coupling the camera system 10 to the computer system 20. The computer system 20 communicates data acquisition parameters (also called data acquisition protocols) selected by a user to the camera system 10 to initiate a particular type of study by the camera system 10. The imaging data from the camera system 10 is then transferred over line 19 to the communications device of the system 20 and this raw gated image data is then forwarded to a post acquisition processing computer system 120. The data acquisition system 20 also comprises a keyboard entry device 21 for a user interface to allow selection and modification of predefined data acquisition parameters which control the imaging processes of the camera system 10. Also coupled to the data acquisition system 20 is a standard color display monitor 28 for display of parameter information and relevant information regarding the particular study underway such as imaging status communicated from the camera system 10 during an imaging session.

For a gated SPECT study a cardiac electrode and signal amplification unit 25 is also coupled to the data acquisition computer system 20, and the cardiac signal goes directly to the acquisition computer 10. This unit 25 is specially adapted to couple with a patient's chest near the heart to receive the heartbeat electrical signal. The unit 25 is composed of well known heartbeat detection and amplification (EKG) components and any of several well known devices can be utilized within the scope of the present invention. In order to perform gated SPECT analysis on the heart, the heartbeat pulse or electrical wave must be studied for each patient, as each patient's cardio rhythm is different. The heartbeat waveform is examined to determine the points within the cycle where the well-known R wave is encountered. The time interval between successive R waves is measured to determine the R—R interval. These points and timing intervals between these points will be used to gate the imaging process of the camera system 10 during the cardiac cycle and particularly at the end-diastole and end-systole interval segments. For a particular projection angle, the system 10 directs the acquired imaging counts to the first segment bin, and upon each successive time interval the image data is directed to a new gated bin. When the R wave is detected once more, the first bin receives the image data again and the process continues through each other segment and associated bin until a new projection angle is encountered. The electrode 25 also is used by the camera system 10 in order to detect the start of a cardiac cycle and gate the camera imaging system appropriately depending on the number of selected segments of the R—R interval used for collection.

Referring still to FIG. 1, the image data is sent from the camera system 10 over line 19 to acquisition system 20 and then over line 22 to the post acquisition processing system 120. This system 120 is responsible for processing, displaying and quantifying certain data acquired by system 10 and system 20. The post acquisition processing system 120 acquires raw image data generated by the camera system 10 and, using user configurable procedures, reconstructs (performs tomography or backprojection) the data to provide a reconstructed volume and from the volume generates specialized planar or volumetric images for diagnosis, including generating and displaying the functional images as described above. In cardiac imaging the generated images or frames represent different slices of the reconstructed heart volume at variable thicknesses in a short axis dimension, a vertical dimension and a horizontal dimension (all three are user configurable) for a number of gated time segments. Therefore, complete three dimensional information can be displayed by display 105 in a two dimensional manner in a variety of formats and orientations including a display providing quantitative information regarding both wall thickening (perfusion) and wall motion (function) of the myocardium under study.

The data acquisition system 20 allows a user via keyboard, touchscreen, or pointer control to select and/or create a predefined set of parameters (or protocols) for direction of a gated SPECT imaging session or other selected study by the camera system 10. FIG. 3 illustrates a parameter interface screen and configurable parameters of a nuclear camera system for data acquisition that are selected and displayed on a screen by the user via keyboard 21. FIG. 3 illustrates some of the parameters that are configurable by the data acquisition system 20. It is appreciated that once set, the configurable parameters can be saved and referenced in a computer file for subsequent recall. The stored parameters or protocol file can then be recalled and utilized for a particular study, thus eliminating the need to again enter the parameters for similar or identical studies. As described in detail below, in a constructed embodiment of the present invention the stored parameters or protocol file can also be modified during the execution of the study by the user. The name of the parameter file shown in FIG. 3 is "GATED SPECT" and is indicated at 300. It is appreciated that the computer system 20, once instructed by the user, will relay the parameters set by the user to the camera system 10 in order to initialize and begin a particular study. The initiation is done by selection of processing command 357. In accordance with the principles of the present invention the parameters are also sent to the camera system after they have been modified by the user during the study. A flowchart depicting the operation of the gamma camera system with dynamically variable parameters is shown in FIG. 3 and will be discussed in detail below. A user interface of this type is thus versatile while at the same time providing a high degree of automation of the execution and modification of selected study protocols.

Figure 4:
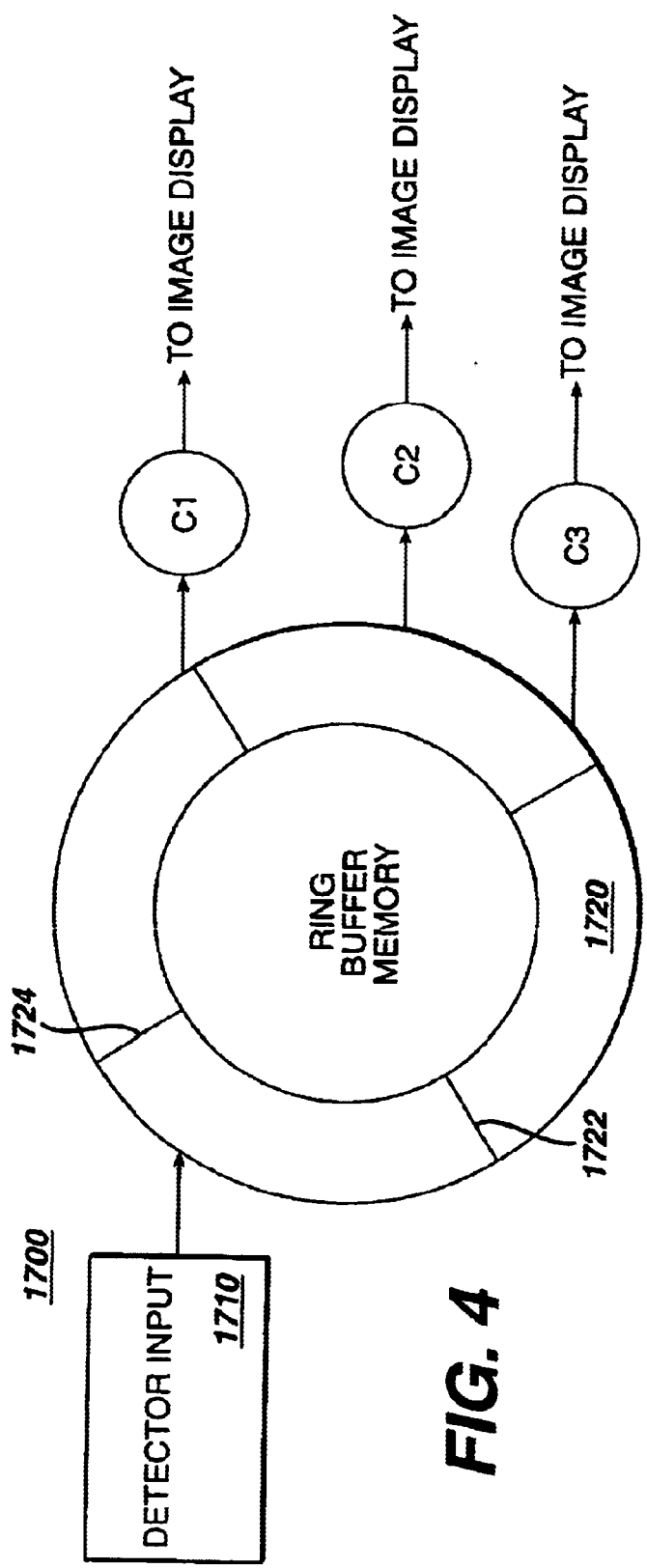
FIG. 4 illustrates in block diagram form a network of the gamma camera which simultaneously processes different data sets during a study.

In a preferred embodiment, the gamma camera system of FIGS. 1–2 is capable of performing several studies simultaneously by use of the data network shown in FIG. 4. The network includes a ring buffer 1720 into which gamma camera data is entered at a high data rate. The data in the illustrated ring buffer 1720 may have a specified start point 1722 and an end point 1724 that may adjust around the ring buffer as data is received and processed. The gamma camera data is entered into the ring buffer by a Producer, one of which is shown at 1700. A Producer is a camera subsystem or data path which enters data into the ring buffer 1720. The Producer illustrated in the drawing is a data stream 1710 from a detector or camera head, which inputs detector data into the ring buffer. Other Producers may provide data from other sources such as stored data sources, for example. Some of the types of data words which are provided by a detector are described in FIG. 6 below.

Accessing the data which traverses the ring buffer 1720 are one or more Consumers. Three Consumers are shown in FIG. 4, and are labeled C1, C2, and C3. A Consumer is a data processor or path or other entity which makes use of some or all of the data in the ring buffer 1720. In the illustrated embodiment each Consumer is an entity conditioned to look for specific characteristics of event data and to read data from the ring buffer selected for a particular type of study. The studies in the following examples are all associated with types of images and hence the Consumers shown in this example read and process selected data into images, which can then be forwarded to an image display. Each Consumer C1, C2 and C3 examines the data in the ring buffer as it passes by its input, and independently reads those data words which are needed for the studies being supported by that Consumer. The Consumers operate both independently and simultaneously, and each can support one or more imaging processes.

Figure 5:
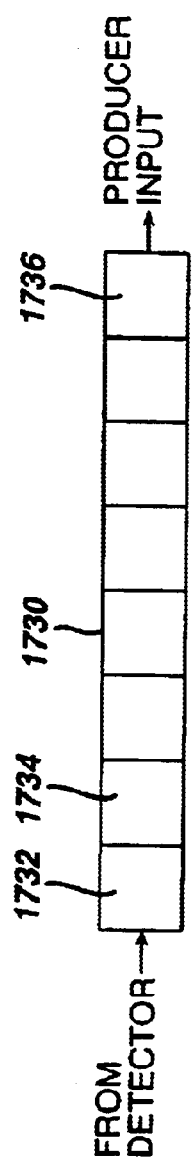
FIG. 5 illustrates a high speed data path from which the Producer of FIG. 4 reads input data.

In a constructed embodiment the data from a detector, being produced in real time as the detector head detects scintillation events, is provided over a high speed data path 1730 as illustrated in FIG. 5. The stream of data words is provided serially from the detector as indicated by sequential data locations 1732, 1734 . . . 1736. The data at the output of the data path 1730 is read by the input of a Producer, which enters the data into the ring buffer 1720.

Figure 6:
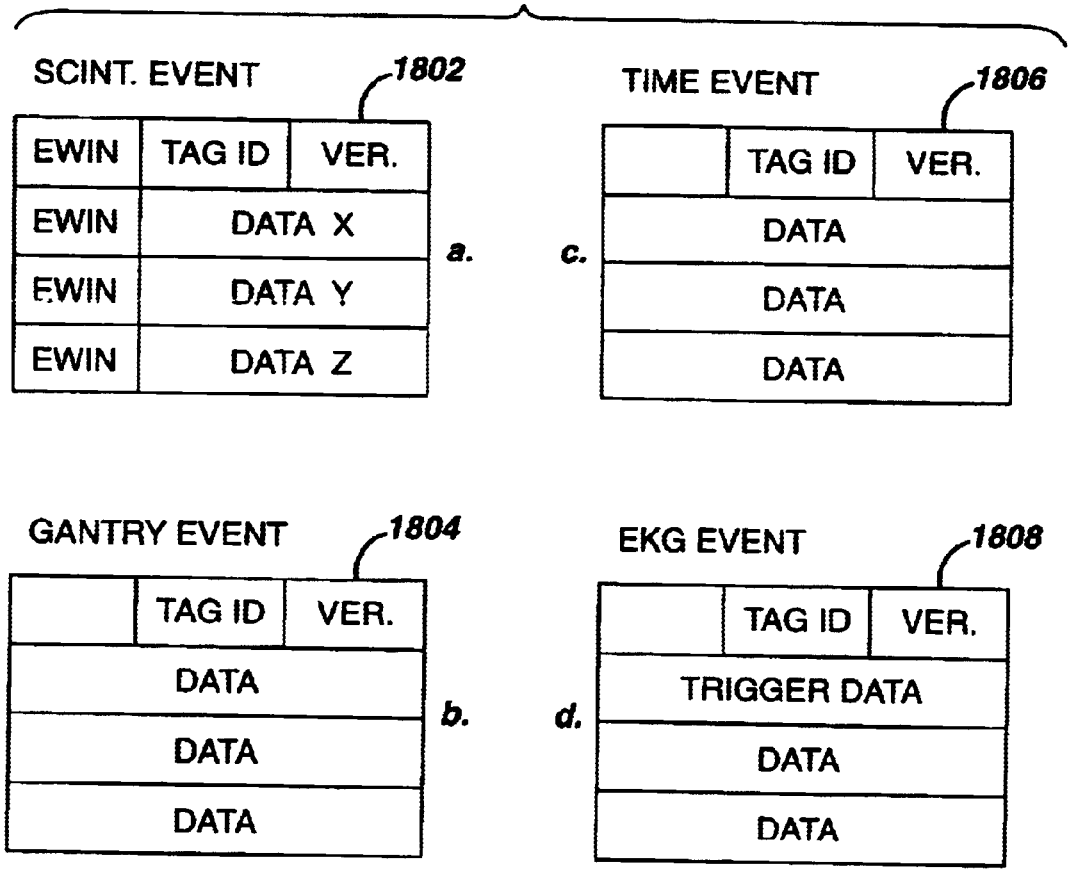
FIGS. 6a–6d illustrate the format of the data used in a constructed embodiment of the present invention.

Examples of the types of event data which may be provided by a detector are shown in FIG. 6. In this example each event word is 64 bits long. The words in this drawing are shown in four lines of sixteen bits each. FIG. 6a illustrates a scintillation event word 1802 with four energy window bytes EWIN of four bits each. The setting of one of these bits denotes one of sixteen energy windows in which the particular scintillation event was acquired. Typically a detector will only produce data for energy windows chosen by the camera operator. The TAG ID and TAG VERSION (VER.) bytes identify the data word as a scintillation event word. The TAG bytes provide information such as the detector number which produced the event. Data X and Data Y provide the x and y coordinate locations on the detector at which the event was sensed. The Data Z byte provides the energy number of the detected event.

FIG. 6b shows a format for a gantry event word 1804. Gantry event words provide information as to the current position of the gantry and hence the locations of the detectors. Gantry event data originates with sensors, controllers, and other devices associated with the gantry or from control programs for the gantry. The illustrated gantry event word 1804 has TAG ID and VER. bytes which identify the word as a gantry event word. The TAG bytes provide information as to the type of information contained in the gantry event word. The last three lines contain the data pertinent to the gantry event.

FIG. 6c gives an example of a time event word 1806. The acquisition system provides these words as time markers so that the other events of the camera can be oriented in time. Time events occur in regular intervals such as once every millisecond. The TAG bytes of the time event word denote the word as a time event word. The rest of the time event word comprises data giving the time information.

FIG. 6d illustrates an EKG event word 1808, which will be produced when a cardiac electrode unit 25 is used for a gated study. The TAG bytes identify the word as an EKG event word. A TRIGGER DATA byte provides information as to the trigger event, and the other data bytes of the EKG event word provide other information pertinent to the EKG event.

Other event words may also be present in the data stream provided by the detectors and entered into the ring buffer 1720. For example Start and Stop event words may be used to indicate the start of an image acquisition session and the conclusion of an image acquisition session.

Different types of studies can be performed with the camera system of the present invention. In a planar or static study the detector is located in a stationary position opposing the patient and event data is gathered without moving the gantry. In a total body or ECT study scintillation events are acquired from a plurality of detector locations either while the gantry moves the detector or when the detector motion stops at a number of incremental positions around the patient. Event acquisitions are repeated for each gantry position based upon the detection of new gantry events by the Consumer. In a constructed embodiment a Consumer provides status of its acquisitions to a control program. When the Consumer has satisfied its needs for new event data at a particular gantry location, this status is reported to the control program. When all Consumers report that they are satisfied, the control program commands the movement of the gantry to the next detector position. When acquisition data has been acquired from all of the gantry positions of the protocol, the study and its acquisition of the simultaneous images are complete.

Three of the parameters commonly used in the protocol of a nuclear medicine study are time, the number of frames acquired, and the count criterion for an image. For example, in a given study the time parameter may be set to scan the patient for ten minutes. In a renal study ten frames may be acquired during the washout of the isotope. In a particular study the clinician may want to detect a maximum of 10,000 counts per image in order to produce a reliable image. Conventionally parameters such as these are set by the clinician as the gamma camera is set up for the desired study. Upon issuance of the processing command by the clinician, the camera commences to carry out the programmed study.

In accordance with the principles of the present invention, acquisition parameters such as these may be modified during the conduct of the study upon input from the clinician when the clinician believes that such changes are warranted. FIG. 3 illustrates one method by which a Consumer may do this. In this process a Consumer is receiving event data words which relate to the imaging procedure being carried out by the Consumer. At step 202 the Consumer selects the event data which is relevant to the study being executed by the Consumer and steers the event data to the appropriate place for its accumulation. At step 204 time is accumulated by reading time event words 1806. At step 206 the number of frames which have been acquired is accumulated. At step 208 the scintillation events received for the image which is currently being acquired are counted and accumulated.

In the following steps the accumulated values are compared with the parameters established by the protocol of the study. In a constructed embodiment these parameters are stored in registers of the data acquisition system 20. The time duration accumulated in step 204 is compared with a time parameter in step 212. The number of frames accumulated in step 206 is compared with a "# frames" parameter in step 214, and the event count accumulated in step 208 is compared with a count parameter in step 216. The result of each comparison is either a "No" when the parameter value has not yet been attained by the accumulated value, or "Yes" when the accumulated value has reached the respective parameter value.

The "Yes" outputs of the comparisons are applied to a step 220 which tests for the satisfaction of one of the parameters. When this test finds that one of the conditions has been satisfied by the receipt of a "Yes" result from the comparison steps, the test issues an output which causes the protocol to go to the next stage of the protocol (e.g., the next gantry position or stage), or indicates that the study is completed.

In accordance with the principles of the present invention, the parameters used in the comparison steps 212, 214, or 216 may be varied by the clinician after the study has begun. For instance, the clinician may decide to increase the time that events are accumulated, the number of frames, or the event count criterion after the study has begun. The new parameter values are input into the camera by means of the user interface of the data acquisition system 20. In a preferred embodiment, before the newly entered or selected parameter values are applied to modify the study, they are analyzed by the data acquisition system to verify that the new parameters can be used effectively at or following the current point in the study. For example, if the clinician changes the time during which event data is to be acquired to eight minutes at a time when event data has been acquired for the previous nine minutes, the system 20 would not change the time criterion, but would terminate the acquisition immediately. Similarly, if the clinician enters a change in the number of frames to be acquired during the second stage of a study after the camera has progressed to the third stage of the study, the system would inform the clinician that the requested change cannot be made, or would simply reject the requested change; a reduction in the number of frames to be acquired after the frames have been acquired can obviously not be accommodated. Changes which have been found to be valid given the current state of the study are then automatically carried out by the data acquisition system 20.

Examples of the use of these capabilities may be applied to the aforementioned clinical examples. In the case of the first example mentioned above in which the time parameter had been initially set for ten minutes, the clinician may observe from the P scope data at the eight minute mark that the uptake of the isotope has been slower than anticipated, and that more time is required to acquire sufficient data for a clinically relevant data set. In such case the clinician may change the time parameter to fourteen minutes, for instance. The data acquisition system would analyze this requested change and determine that such a change can be validly made at this point in the study. The new time parameter would be applied to the system and the time comparison 212 would thus not issue a "Yes" result until the acquisition had continued for fourteen minutes. The clinician may thus have transformed a potentially inconclusive study into one which produces clinically diagnostic images.

In the example cited above for a renal study which is set up to acquire a certain number of frames, the clinician may have originally set up the camera for a dynamic study done in three stages. In the first stage, as the isotope is applied to the patient and flows into the kidneys, the study may call for the acquisition of 60 frames at ten seconds per frame. During a second stage, as the isotope washes out of the kidneys, the protocol may call for the acquisition of 20 frames at twenty seconds per frame. During a third stage, as washout is completed, ten frames may be acquired at one minute per frame. But suppose that the clinician observes that the washout of the isotope is not occurring as rapidly as anticipated. In such case the clinician may command that 30 frames be acquired during the third stage, in which case the frame comparison step would compare the number of frames acquired during the third stage against the new value for the number of third stage frames, and would not end the stage until the new number of frames has been acquired.

In either of the above examples, the clinician may decide that a greater or lesser number of scintillation event counts are required in order to produce clinically relevant images. A change in the counts parameter is made, and the accumulation of counts for the images is compared with the new counts parameter. Once again, the clinician has dynamically intervened to transform a potentially inconclusive study into one with diagnostically useful images, or has shortened the duration of the study for the patient.

What is claimed is:

1. A gamma camera comprising:
   a detector which acts to acquire scintillation event data;
   an event data processor coupled to the detector which is responsive to the event data to produce image information;
   a camera system controller, responsive to study parameters, which acts to control the camera to perform a desired nuclear study; and
   a user input, coupled to the controller, which enables user selection of a study parameter,
   wherein the user input is operable during the conduct of a study to enable the user to modify the study parameter.

2. The gamma camera of claim 1, wherein the user input is operable while the detector is acquiring scintillation event data to modify the conduct of the study.

3. The gamma camera of claim 1, further comprising a gantry, coupled to the detector, which acts to move the detector from an initial position to a final position during the conduct of a study.

4. The gamma camera of claim 1, wherein the study parameter which is modified is the time of event data acquisition.

5. The gamma camera of claim 1, wherein the study parameter which is modified is the number of frames acquired during the study.

6. The gamma camera of claim 1, wherein the study parameter which is modified is the count criterion for data acceptance.

7. The gamma camera of claim 1, wherein the camera system controller acts to control the camera to perform the desired nuclear study in a series of stages; and
   wherein the user input enables the user to modify a study parameter of a stage which has not yet been executed during the conduct of the study.

8. The gamma camera of claim 7, wherein the camera system controller is responsive to the modification of a study parameter during the conduct of the study to ascertain whether the modified parameter can be prospectively utilized.

9. A method of operating a gamma camera to conduct a nuclear study comprising:
   preconditioning the camera with parameters which govern the conduct of the study by the camera;
   commanding the camera to begin the study in accordance with the parameters; and
   prior to the conclusion of the study, commanding the camera to complete the study in accordance with a modified parameter.

10. The method of claim 9, wherein the parameters include at least one of the time duration of the study, the number of frames acquired during the study, and the count criterion for data acceptance,
    wherein at least one parameter is modified prior to completion of the study.

11. The method of claim 9, further comprising:
    verifying that a modified parameter can be prospectively utilized during the completion of the study.

* * * * *